United States Patent [19]

Stoller et al.

[11] Patent Number: 4,799,883
[45] Date of Patent: Jan. 24, 1989

[54] ORTHODONTIC MIRROR IMAGE BRACKETS TO REMOVABLY RECEIVE THE END PORTIONS OF LINGUAL ARCH WIRES

[76] Inventors: Arnold E. Stoller, 2150 Shore Ave., Freeland, Wash. 09249; John L. Stoller, 901 Sunset Dr., Blue Bell, Pa. 19422

[21] Appl. No.: 30,442
[22] Filed: Mar. 25, 1987
[51] Int. Cl.$^4$ .............................................. A61C 7/00
[52] U.S. Cl. .......................................... 433/17; 433/11
[58] Field of Search ................................... 433/17, 11

[56] References Cited

U.S. PATENT DOCUMENTS

| | | | |
|---|---|---|---|
| 1,481,861 | 1/1924 | Eaton | 433/10 |
| 1,764,067 | 6/1930 | Craigo | 433/14 |
| 1,905,877 | 4/1933 | Aderer | 433/17 |
| 3,043,007 | 7/1962 | Wallshein | 32/14 |
| 3,052,028 | 9/1962 | Wallshein | 433/11 |
| 3,335,496 | 8/1967 | Andrews et al. | 32/14 |
| 3,724,074 | 4/1973 | Wallshein | 433/11 |
| 4,167,813 | 9/1979 | Forster | 32/14 A |
| 4,192,070 | 3/1980 | Lemchew et al. | 433/11 |
| 4,483,674 | 11/1984 | Schütz | 433/22 |
| 4,498,867 | 2/1985 | Kesling | 433/17 |
| 4,511,331 | 4/1985 | Scebold et al. | 433/17 |
| 4,547,153 | 10/1985 | Taylor | 433/11 |
| 4,561,844 | 12/1985 | Bates | 433/14 |
| 4,571,179 | 2/1986 | Balenseifen | 433/20 |
| 4,573,913 | 3/1986 | Creekmore | 433/12 |

FOREIGN PATENT DOCUMENTS 685981 12/1939 Fed. Rep. of Germany ......... 433/17

Primary Examiner—Robert Peshock
Attorney, Agent, or Firm—Shlesinger, Arkwright & Garvey

[57] ABSTRACT

Mirror image orthodontic brackets of an overall elongated block configuration are provided for attachment to bands, in turn secured to molars, to receive respective horizontal ends of lingual arch wires terminating in ninety degree bend portions. The overall elongated block configuration has: one medial surface for attachment to a band to be secured to lingual side of a molar; one interrupted occlusal surface presenting a longitudinal slot to receive a horizontal end of a lingual arch wire; one forward, i.e., mesial, interrupted surface presenting the entry of the longitudinal slot; one rear, i.e. distal interrupted surface presenting the exit of the longitudinal slot; one interrupted surface presenting the exit of a vertical slot or hole, which in turn joins the longitudinal slot, and upon the securement of the lingual arch wire receives the ninety degree bent portion; and one interrupted lingual surface opposite the surface to be attached to the band presenting a flexure portion to move upon the insertion and withdrawal of a horizontal end of a lingual arch wire, or presenting a recessed portion to accommodate a limited deflection of the lingual arch wire, upon the insertion and withdrawal of this wire and a protuberance in the longitudinal slot located by the flexure portion, or by the recessed portion in another bracket to provide a snap in and snap out function to receive and to discharge the horizontal end of a lingual arch wire, whereby these shaped lingual arch wires are snapped into place using the longitudinal slot and the intersecting vertical slot, and are then held securely in respect to all three geometric planes to provide their accurate control in respect to the molars, with the lingual arch wire being adapted with accuracy, without special pliers at the dental chair locale, saving time, effort, and expense.

33 Claims, 2 Drawing Sheets

ORTHODONTIC MIRROR IMAGE BRACKETS TO REMOVABLY RECEIVE THE END PORTIONS OF LINGUAL ARCH WIRES

BACKGROUND OF THE INVENTION

The need for a lingual arch wire with supports thereof has long been recognized in dentistry. This strong wire, when supported on molars has a variety of uses, such as to:

1. Maintain space when teeth are prematurely lost;
2. Retain arch size during and after orthodontic therapy;
3. Serve as a base for attaching auxiliary wires for tooth movement;
4. Provide anchorage, total or supplemental, for tooth movement; and
5. Regulate molar movement in all planes.

The lingual arch wires and their supports, which are used currently and have been employed by orthodontists for over three quarters of a century, should not be confused with the recent innovation of placing attachments of orthodontic brackets on the lingual surfaces of all the teeth in a dental arch to be regulated. These appliances are referred to as "Lingual Appliances".

Originally, the round lingual arch wire was fixed, by soldering it to the molar bands, in turn cemented to molars. To make adjustments of the lingual arch wire or to add auxiliaries to it, the molar bands to which it was soldered had to be removed from the molars and recemented each time. This time consuming and cumbersome approach to manipulating the lingual arch wire with or without auxiliaries resulted in a search for orthodontic devices, which could be designed to secure the lingual arch wire in a very fixed way, and yet have it be quickly and easily removed.

Such orthodontic devices were said to make the lingual arch wire "fixed-removable". One of the first devices for a "fixedremovable" lingual arch wire was designed by John V. Mershon. The Mershon device was a bracket which consisted of a half round tube soldered vertically to a molar band. Then a half round wire dimensioned to fit the half round tube was soldered on the lingual arch wire. Thereafter, when the half round wire was fitted to the half round tube on the molar band, one end of the lingual arch wire was secured.

Later, Dr. A. Edel formed a lingual arch wire receiving bracket, which had two vertical round tubes soldered parallel to each other on the molar band. A round wire staple was adapted to fit simultaneously into the vertical tubes. This staple was then soldered to the lingual arch wire and then used in securing one end of the lingual arch wire.

Walter H. Ellis attempted to improve on Dr. Edel's bracket by using a specially formed continuous arch wire, thus eliminating a soldering operation. An oval tube was soldered vertically to the lingual of the molar band. The terminal end of the lingual arch wire was fabricated with a short, closed loop, which fitted in the vertical oval tube.

All of these prior devices, inclusive of their brackets did function, but their negative factors were: the difficulty of their fabrication, and their frequency of breakage, which was all too frequent.

Spencer R. Atkinson designed a lingual arch bracket with a horizontal sheath, which is currently available. The terminal end of the lingual arch wire was recurved on itself and then was retained by friction in the horizontal sheath. The negative factors were and are; special pliers are needed to form the recurved end; and also a dentist may experience difficulty in placing and removing the recurved ends in the respective horizontal oriented sheath.

The Gashgarian Palatal Bar described by Fredrico V. Tent has a horizontal molar sheath similar to Atkinson's bracket. The arch wire is oriented palatally after it leaves the sheath. The arch wire is prefabricated and is presently available in four different sizes.

Wilson has made and still makes a prefabricated lingual arch wire with closed loops. These closed loops fit precisely into two vertical tubes on respective molar bands. They may be obtained from Rocky Mountain Orthodontic Supply Company in Denver, Colo.

Although these prior brackets and devices were and are effective in positioning and securing lingual arch wires, a simple and more efficient approach to attaching a lingual arch wire to the molars is still needed.

SUMMARY OF THE INVENTION

The mirror image orthodontic brackets are simple and conveniently used, and considered "fixed-removable". The advantages realized in using these mirror image orthodontic brackets are:

1. No special pliers are needed to construct or manipulate the lingual arch wire;
2. The lingual arch wire is inserted and removed with respect to the occlusal direction;
3. The horizontal orientation of the bracket eliminates lingual arch wire breakage or other installation breakage;
4. The snap-lock is positive and retains the lingual arch wire firmly in the bracket in its fixed-removable position;
5. The snap out unlocking of the lingual arch wire is simple and easy;
6. The lingual arch wire may be formed and accurately placed in the patient's mouth, when the dentist remains by the dental chair;
7. Laboratory procedures are eliminated; and
8. These mirror image orthodontic brackets via their securement of the lingual arch wire control molar tooth movement in all geometric planes.

When these mirror image orthodontic brackets are welded or soldered to the lingual surface of molar bands, which are in turn cemented to molars, they are then ready to fixed-removably receive a lingual arch wire, which has its respective ends terminating in ninety degree bend portions. In reference to a patient's lower jaw and the patient's molars on the left side of his or her mouth, as shown in FIG. 2, a mirror image orthodontic bracket has an overall elongated block configuration. One essentially vertical side or surface, designated as the medial surface and generally not interrupted, is provided for soldering or spot welding the attachment to a molar band. One interrupted occlusal surface is provided for presenting the entrance to a longitudinal slot which is made in this bracket to receive a horizontal end of a lingual arch wire. In respect to the postioning of a mirror image orthodontic bracket, as shown in FIG. 2, this interrupted surface is positioned to be a top or occlusal surface, and the lingual arch wire is moved downwardly, so the end thereof will fit into the longitudinal slot. One forward, i.e. mesial, interrupted surface is provided to present an entry of this longitudinal slot.

One rear, i.e. distal, interrupted surface is provided to present an exit of the longitudinal slot. One interrupted surface, opposite the occlusal surface, is provided in one orientation to present the exit below of a vertical slot or hole, which in turn above at its entrance, joins the longitudinal slot. This entrance of the vertical slot or hole interrupts the occlusal interrupted surface toward or nearer the distal end of the longitudinal slot. In FIG. 2, this surface, opposite the occlusal surface, is positioned to be the bottom surface. Upon securement of the lingual arch wire, this vertical slot or hole receives its ninety degree bend portion.

Then there is one interrupted vertical surface referred to as the lingual surface, which as viewed in FIG. 2, would be the outside vertical surface, which is opposite to the vertical side or surface designated as the medial surface which is soldered or welded to the molar band. Its interruptions present a flexure portion, or flexure portions, which resiliently, transversely, move, upon the snap in insertion and snap out withdrawal of the horizontal end of the lingual arch wire, which terminates in a ninety degree bend portion. Also a protuberance is formed in the longitidunal slot and spaced with respect to the flexure portion, or flexure portions, to aid in providing the snap in and snap out functions, undertaken during the installation and removal of the horizontal ends of the lingual arch wire.

The lingual arch wires, considered to be fixed-removable, are securely held in place in respect to all three geometric planes to provide accurate control of the molars and the lingual arch wire itself. Each lingual arch wire is adapted accurately, without using special pliers at the dental chair locale in the presence of the patient, thereby saving time, effort and expense.

BRIEF DESCRIPTION OF THE DRAWINGS

The orthodontic mirror image brackets in several embodiments are illustrated in the drawings in respect to their several in use positions, wherein the lingual arch wire or portions thereof are also illustrated, inclusive of an orthodontic band or portions thereof. In the drawings.

DESCRIPTION OF THE PREFERRED EMBODIMENTS

The orthodontic mirror image brackets 20, 21, illustrated throughout the drawings, when installed in a person's mouth, via their securement to respective molar bands 22, which in turn are secured to a patient's molars 24, make it conveniently and quickly possible for a dentist, who practices orthodontics, i.e. an orthodontist, to fit a lingual arch wire 26, without using special pliers, yet with accuracy, while at a dental chair locale, to a patient, thereby saving time, effort, and expense.

Figure 1:
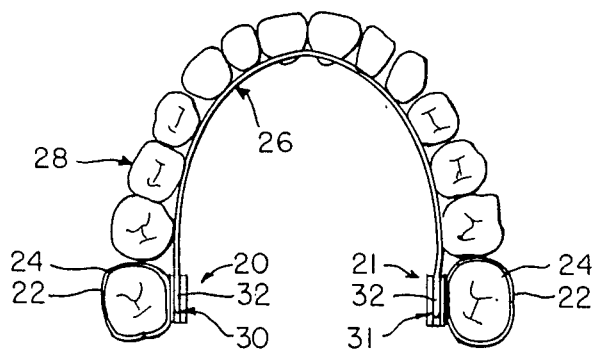
FIG. 1 is an occlusal view of a person's upper full dental arch showing how the lingual arch wire is positioned and held in place by using the orthodontic mirror image brackets, in turn secured to the orthodontic bands, in turn secured to the patient's molars.

In the occlusal view of FIG. 1 of a person's full upper dental arch 28, a respective pair of orthodontic mirror image brackets 20, 21 are shown, one 20 on the left being the mirror image of the other 21 on the right. Each bracket 20, 21 is secured, such as by spot welding or soldering, to a standard molar band 22. Each band 22 in turn, is cemented to a second molar 24, as shown, or to a first molar, not shown. These brackets 20, 21 receive the respective ends 30, 31 and the end horizontal portions 32 of the lingual arch wire 26, which also has short perpendicular portions 34, and ninety degree bend portions 36.

Figure 2:
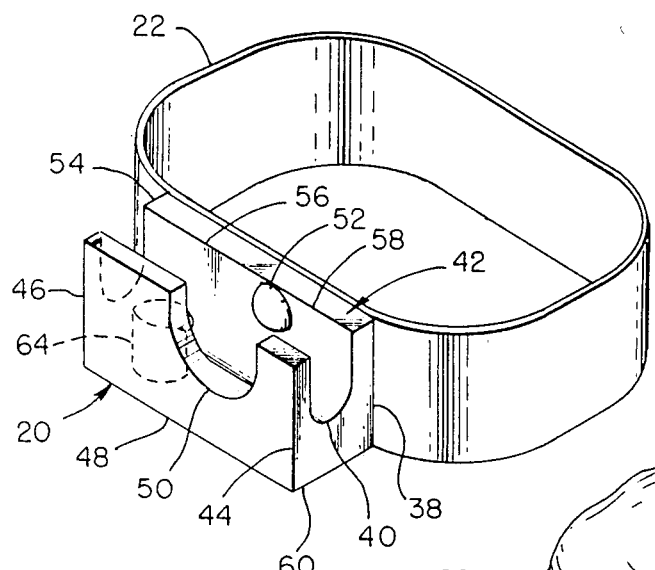
FIG. 2 is an isometric view of a sole molar locale of a person's dental arch, illustrating how an orthodontic mirror image bracket is secured to an orthodontic molar band, which in turn is secured to the molar.
Figure 3:
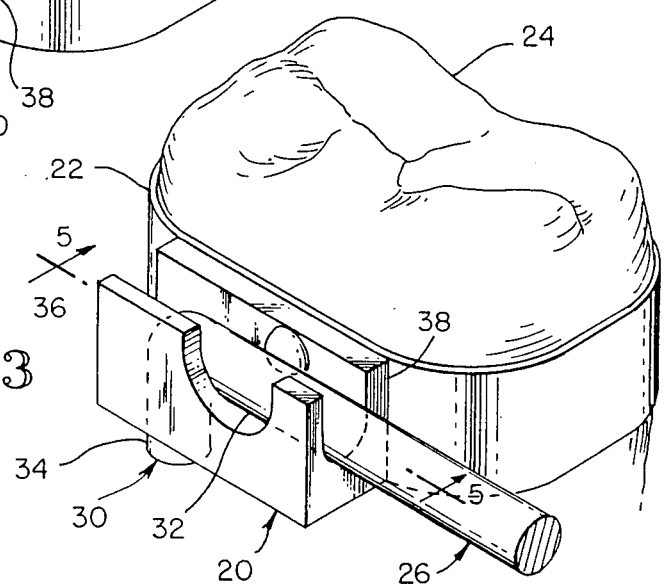
FIG. 3 is an isometric view of a sole molar locale of a person's dental arch, illustrating how an orthodontic mirror image bracket is secured to an orthodontic molar band, which in turn is secured to the molar, and further indicating how lingual arch wire, which has a ninety degree bend end portion, is snapped into place, in its fixed-removable position, within the orthodontic mirror image bracket.

How these respective overall end portions 30, 31 of the lingual arch wire 26 are fixed-removably received and held in the brackets 20, 21, in respect to a preferred embodiment, is illustrated in FIGS. 2, 3, 4, 5, and 6. In FIG. 2, the overall elongated metal block configuration bracket 20, serving as the orthodontic mirror image bracket 20, has one medial surface 38 of its longest dimension, from mesial to distal, arranged horizontally and spot welded or soldered to an adjacent molar band 22. This medial surface 38 is preferably uninterrupted. The molar band 22, in turn, is cemented to a molar 24.

In respect to the further formation of the orthodontic mirror image bracket 20, a horizontal slot 40 is formed in the entire length of the then interrupted occlusal surface 42 of the bracket 20, from the mesial face 44 to the distal face 46 in the horizontal plane. This slot 40 is sized and made deep enough to accurately accommodate the diameter of the lingual arch wire 26 throughout its end horizontal portion 32. The mesial face 44 and the distal face 46 are both interrupted by this horizontal slot 40.

The outside wall 48 of the bracket 20 having the lingual surface is cut away forming the open slot 50, which extends to the bottom of the horizontal slot 40, which in turn only extends part way through the bracket 20. A locking protuberance 52 is positioned on the inside wall 54, on its lingual surface 56, to project into the horizontal slot 40 near its entry 58. When the end horizontal portion 32 of the lingual arch wire 26 is moved into place in the horizontal slot 40, the slotted outside wall 48 by the open slot 50 flexes, and the horizontal portion 32 of the lingual arch wire 26 flexes permitting the passage of this end horizontal portion 32 past the locking protuberance 52 for fixedremovable securement in the horizontal slot 40.

Figure 4:
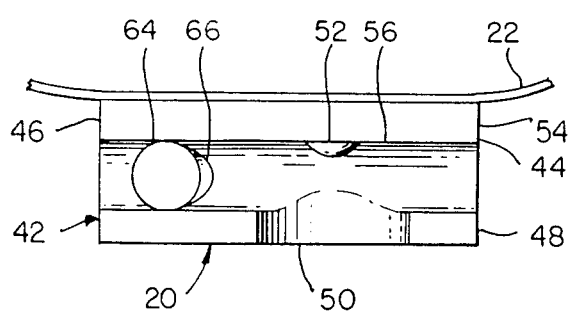
FIG. 4 is a top view or occlusal view of an orthodontic mirror image bracket, secured to an orthodontic molar band, before receiving the end of the lingual arch wire.
Figure 5:
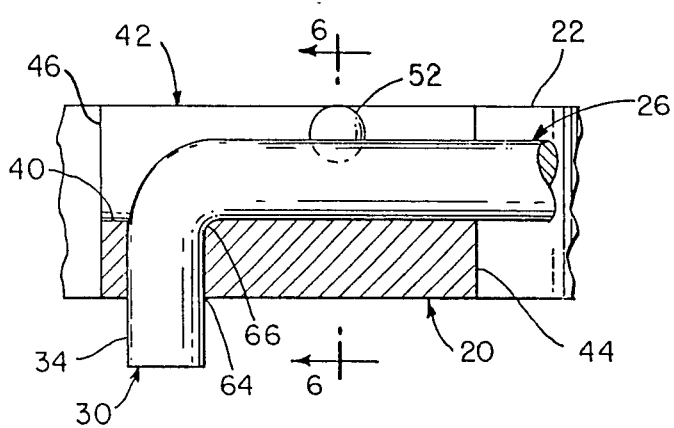
FIG. 5 is a side view or lingual view of an orthodontic mirror image bracket, with some portions removed, showing how the ninety degree bend end portion and the horizontal end portion of the lingual arch wire are secured in the fixed-removable position, indicating the horizontal slot, the vertical hole, and the locking protuberance, but not indicating the cut away portion creating the flexure capability of the lingual arch wire and/or the outside wall of the bracket.
Figure 6:
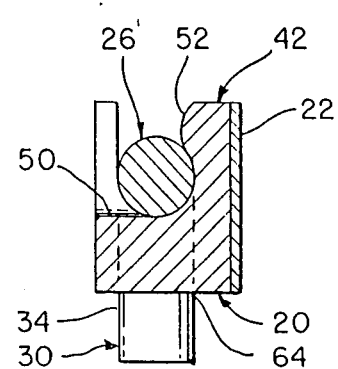
FIG. 6 is a sectional view taken on line 6—6 of FIG. 5 of an orthodontic mirror image bracket, illustrating how it is secured to a molar band, and how it receives the ninety degree bend end portion and the horizontal end portion of the lingual arch wire, by utilizing the horizontal slot, the vertical slot or hole, the locking protuberance, and the cut away portion, in part, creating the flexure capability of the lingual arch wire and/or the outside wall of the bracket, whereby the lingual arch wire is secured in its fixed-removable position.

The long horizontal surface 60 of the bracket 20, 21 opposite to the long occlusal surface 42 is interrupted only by the exit of a vertical hole 64, which extends from the horizontal slot 40 to this surface 60 also known as the gingival face 60. The ends 30, 31 of the lingual arch wire 26, each having a ninety degree bend portion 36, and continuing on as a short perpendicular portion 34, are inserted into the vertical hole or slot 64. A half round bevel portion 66, as shown in FIG. 4, is formed between the hole 64 and the horizontal slot 40 to accommodate the ninety degree bend portion 36 of the lingual arch wire 26. Preferably the short perpendicular portion 34 extends in part beyond the surface 60, when the lingual arch wire 26 is inserted into the bracket 20.

Upon each insertion of this short perpendicular portion 34 into the vertical hole 64, both mesial and distal longitudinal movements of the lingual arch wire 26 are prevented. Also the rotation of the lingual arch wire 26 is prevented, as long as the lingual arch wire 26 remains snapped into place in its fixedremovable position is horizontal slot 40.

Figure 7:
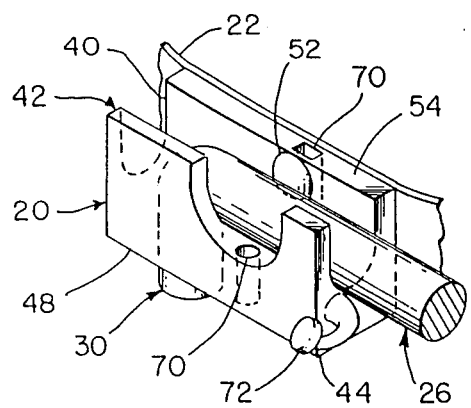
FIG. 7 is an isometric view somewhat similar to FIG. 3 of another embodiment of an orthodontic mirror image bracket, indicating how holes are provided to receive portions of ligatures and how hooks are provided to receive portions of intermaxillary elastics.

In respect to other embodiments, the orthodontic mirror image bracket 20 illustrated in FIG. 7, has a vertical hole 68 in the outside wall 48, and a vertical hole 70 in the inside wall 54, which are positioned to receive a passing ligature, not shown, to supplement the locking mechanism. Also a hook 72 is attached to the mesial face 44, i.e. front end 44, of the bracket 20, to facilitate the application of intermaxillary elastics, not shown.

Figure 8:
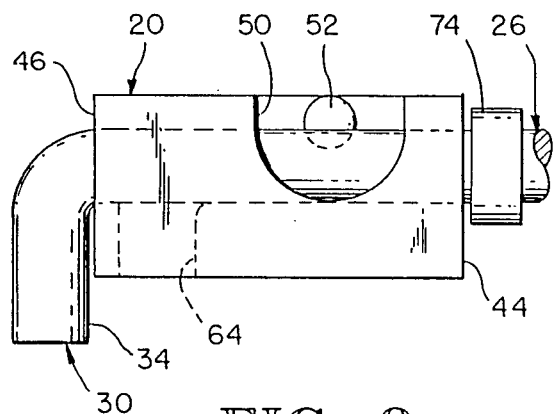
FIG. 8 is a side view or lingual view of an orthodontic mirror image bracket indicating a different way of securing the end of the lingual arch wire, whereby the ninety degree bend end is turned down, as shown, beyond the rear or distal end of this bracket to block its movement back out of a patient's mouth, and the longitudinal end has a stop placed on its mesial end to keep the lingual arch wire from moving farther distally into a patient's mouth, yet the lingual arch wire may allow, if desired, the molar rotation on the arch wire, serving as the axis of rotation, with respect to the adjacent molar, because the ninety degree bend end is not confined by the vertical hole in this bracket; however, the lingual arch wire is still fixed-removably held.

In respect to other methods of usage, there are other ways of positioning the respective ends 30, 31 of the lingual arch wire 26, as shown in FIG. 8, wherein the short perpendicular portion 34 is positioned beyond the vertical hole 64, to extend along the distal face 46, i.e. back end 46, of the orthodontic mirror image bracket 20. This assembly permits the molar 24, having its molar band 22 attached to the bracket 20 to rotate around the lingual arch wire 26. In some patient treatments some relatively minor rotational movement is desirable. The short perpendicular portion 34 in this position prevents mesial migration of the lingual arch wire 26. Then a stop 74 is placed on the lingual arch wire 26 nearby the mesial face 44 of the bracket 20 to prevent the distal migration of the lingual arch wire 26.

Figure 9:
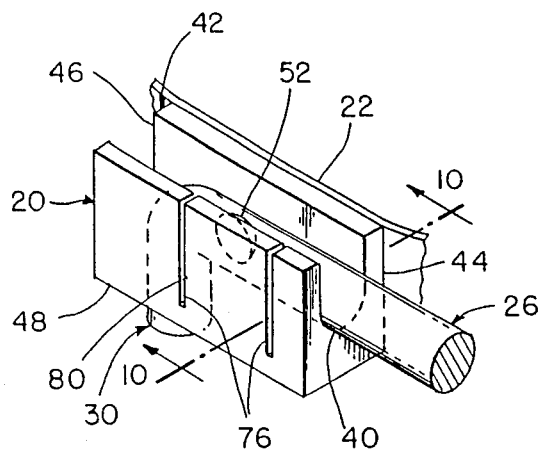
FIG. 9 is an isometric or lingual view, somewhat similar to FIG. 3, showing, however, another embodiment of an orthodontic mirror image bracket, indicating the use of two spaced slots to create a flexure portion between them, which also has an integral locking protuberance, and whereby the lingual arch wire is fixed-removably held in this bracket.
Figure 10:
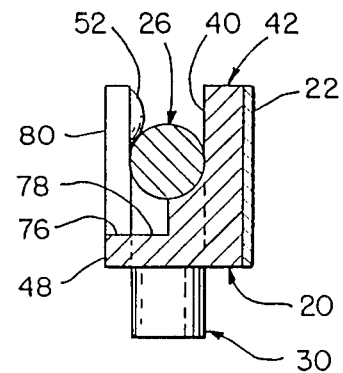
FIG. 10 is a sectional view, taken on line 10—10 of FIG. 9 somewhat similar to FIG. 6, of the embodiment of the orthodontic mirror image bracket shown in FIG. 9, indicating the transverse extent of the two spaced slots, which create the flexure portion used during the securement and release of the fixed-removably held lingual arch wire, and indicating the placement of the locking protuberance on the flexure portion.

Continuing in respect to other embodiments, an orthodontic mirror image bracket 20 is illustrated in FIGS. 9 and 10, wherein the flexure of the outer wall 48 is created by making two spaced vertical cuts 76. They extend beyond the bottom of the horizontal slot 40. They also extend toward the middle of the bracket 20 to create a volume referred to as a well 78, or cellar well 78. The outer wall portion between these cuts 76, which flexes very well, is referred to as the spring lock segment 80.

The locking protuberance 52, in this embodiment of FIGS. 9 and 10, is positioned on this spring lock segment 80. When the lingual arch wire 26 is entered into the horizontal slot 40, its bearing against the locking protuberance 52, moves the spring lock segment 80 outwardly, clearing the way for the complete entry of the lingual arch wire 26. The celler well 78, especially illustrated in FIG. 10, increases the flexure capability of the spring lock segment 80. After the passing of the lingual arch wire 26, the spring lock segment 80 returns to its initial position, placing the locking protuberance 52 over sufficient portions of the lingual arch wire 26, to fixed removably hold the lingual arch wire 26 in place, until it is intentionally withdrawn by an orthodontist.

The use of a selected embodiment of the mirror image orthodontic brackets 20, 21 arranged in pairs with molar bands 22 and a lingual arch wire 26 gains many advantages for an orthodontist, with resulting savings of cost and time. Some of the outstanding advantages are:

1. No special pliers are needed to construct or manipulate the lingual arch wire;
2. The lingual arch wire is inserted and removed with respect to the occlusal direction;
3. The horizontal orientation of the bracket eliminates lingual arch wire breakage or other installation breakage;
4. The snap-lock is positive and retains the lingual arch wire firmly in the bracket in its fixed-removable position;
5. The snap out unlocking of the lingual arch wire is simple and easy;
6. The lingual arch wire may be formed and accurately placed in the patient's mouth, when the dentist remains by the dental chair;
7. Laboratory procedures are eliminated; and
8. These mirror image orthodontic brackets via their securement of the lingual arch wire control molar tooth movement in all geometric planes.

We claim:

1. An orthodontic bracket for connection with an orthodontic wire, comprising:
   a. a body including first and second spaced sidewall means, first and second spaced endwalls disposed therebetween and top and bottom surfaces;
   b. a first slot disposed between said sidewall means and extending from said top surface and at least one of said endwalls of providing an entrance to said slot through said one endwall;
   c. one of said sidewall means for attachment to a support;
   d. means operably associated with the other of said sidewall means for permitting said other sidewall means to flex;
   e. means extending from one of said sidewall means and into said first slot for overlying and thereby locking an orthodontic wire therein; and,
   f. means operably associated with the other of said endwalls for engaging an orthodontic wire and preventing axial displacement thereof along said first slot.
2. The bracket of claim 1, wherein:
   a. said overlying means including a protruberance.
3. The bracket of claim 2, wherein:
   a. said protuberance is substantially hemispherical.
4. The bracket of claim 1, wherein:
   a. said permitting means includes at least a second slot extending from said top surface and terminating short of said bottom surface.
5. The bracket of claim 4, wherein:
   a. said second slot is substantially semicircular.
6. The bracket of claim 4, wherein:
   a. a third slot is disposed in said other sidewall means parallel to said second slot.
7. The bracket of claim 1, wherein:
   a. said means for engaging includes an opening in said bottom surface communicating with said first slot for receiving an end portion of an orthodontic wire therein.
8. The bracket of claim 7, wherein:
   a. said opening disposed proximate the other of said endwalls.
9. The bracket of claim 1, wherein:
   a. said overlying means extending from said one sidewall means.
10. The bracket of claim 1, wherein:
    a. said overlying means extending from said other sidewall means.
11. The bracket of claim 6, wherein:
    a. said overlying means extending from said other sidewall means and disposed between said second and third slots.
12. The bracket of claim 1, wherein:
    a. said first slot extending through said other endwall.
13. The bracket of claim 12, wherein:
    a. said means for engaging includes an opening in said bottom surface is disposed proximate said other endwall and communicates with said first slot.
14. The bracket of claim 1, further comprising:
    a. a molar band is secured to said one sidewall means for permitting operable securement of said body to a molar.
15. The bracket of claim 1, wherein:
    a. said overlying means is integral with said one sidewall means.
16. The bracket of claim 1, wherein:
    a. the body is a parallelepiped.
17. The bracket of claim 1, wherein:
    a. a second slot is disposed in said body proximate the sidewall carrying said means for overlying, said second slot has an axis extending generally transverse to the said first slot.
18. An orthodontic bracket, comprising:
    a. a band for being mounted to a molar;
    b. a parallelepiped having a first slot therein extending between spaced first and second sidewalls thereof and from a first endwall thereof for receiving an orthodontic wire therein, said first sidewall is secured to said band;
    c. means operably associated with said second sidewall for permitting flexing thereof;
    d. means extending from one of said sidewalls and into said first slot for overlying and thereby locking an orthodontic wire therein; and,
    e. means operably associated with said first slot for engaging an end portion of an orthodontic wire positioned in said slot and for preventing the orthodontic wire from being longnitudinally withdrawn from said first slot.
19. The bracket of claim 18, wherein:
    a. said engaging means including an opening through said parallelepiped communicating with and extending generally transverse to said first slot.
20. The bracket of claim 19, wherein:
    a. said opening is disposed opposite to a second endwall of said block and extends generally transverse to said first slot, said second endwall being spaced from said first endwall.
21. The bracket of claim 18, wherein:
    a. a second endwall is spaced from said first endwall and has an exterior surface; and,
    b. said first slot extends through said second endwall so that an orthodontic wire may engage said exterior surface and thereby be prevented from being withdrawn longitudinally through said first slot.
22. The bracket of claim 18, wherein:
    a. said overlying means including a protuberance.
23. The bracket of claim 22, wherein:
    a. said protuberance extending from said first sidewall.
24. The bracket of claim 22, wherein:
    a. said protuberance extending from said second sidewall.
25. The bracket of claim 22, wherein:
    a. said protuberance is substantially hemispherical.
26. The bracket of claim 18, wherein:
    a. said flexing means including at least a second slot in said second sidwall.
27. The bracket of claim 26, wherein:
    a. said second slot is semicircular.
28. The bracket of claim 26, wherein:
    a. said second slot is straight.
29. The bracket of claim 28, wherein:
    a. a third slot is disposed in said second sidewall parallel to said second slot.
30. The bracket of claim 22, wherein:
    a. said protuberance is integral with the associated sidewall.
31. The bracket of claim 30, wherein:
    a. said parallelepiped comprised of metal.
32. The process for securing an orthodontic wire within the mouth of a patient, comprising the steps of:
    a. providing a parallelepiped body having a slot extending between spaced first and second sidewalls and from a first endwall thereof and with means operably associated with the second sidewall for permitting flexing thereof and with means extending from one of the sidewalls and into the slot for locking an orthodontic wire therein and further including an opening in a bottom wall of the body extending transverse to the slot for receiving therein and thereby preventing the wire from being withdrawn longitudinally through the slot;

b. securing the body to a tooth;

c. positioning an orthodontic wire in the mouth of a patient; and, d. overlying a portion of the wire with said slot and aligning an end portion of the wire with the opening and forcing the wire portion into the slot until the locking means overlies the wire portion and locks the wire therein and the end portion is received in the opening.

33. Mirror image brackets, for use in orthodontic dentistry, are provided for solder or welded attachment to bands, in turn to be cemented to molars, to receive the respective horizontal ends of lingual arch wires terminating in ninety degree bend portions, with the horizontal ends being snapped into and out of the mirror image brackets, each of which is of an overall elongated block configuration having:

one uninterrupted medial surface for soldering attachment to a band to be cemented to the lingual side of a molar;

one interrupted occlusal surface presenting a longitudinal slot to receive a horizontal end of a lingual arch wire;

one forward, i.e. mesial, interrupted surface presenting the entry of the longitudinal slot;

one rear, i.e. distal, interrupted surface presenting the exit of the longitudinal slot;

one interrupted surface, opposite to the occlusal surface, presenting the exit of a vertical slot, which in turn joins the longitudinal slot, and upon securement of the lingual arch wire receives the ninety degree bend portion;

one lingual interrupted surface opposite the uninterrupted medial surface having an access to the longitudinal slot and thereby providing flexure of the overall elongated block configuration and flexure of the lingual arch wire at this locale;

a protuberance extending a portion of the way across the longitudinal slot, serving as the locale of the snap in and snap out of a horizontal end of a lingual arch wire, with the snap in and snap out function also being served by the flexure of the one lingual interrupted surface having access to the longitudinal slot;

two spaced small linear openings extend through the one lingual interrupted surface to provide access to the longitudinal slot and create a flexure portion between these two spaced small linear openings;

whereby, in conjunction with a mirror image bracket, soldered or welded to a band cemented on the lingual side of a molar on the opposite side of a person's mouth, serve to receive the respective ends of a lingual arch wire, keeping their respective combinations of the horizontal end portion and the ninety degree bend end portion in plane horizontally, vertically and non-rotatably, as the positioning of the opposite molars are substantially maintained by the active lingual arch wire, mirror image brackets, and the bands.

* * * * *